(12) United States Patent
Jabri et al.

(10) Patent No.: US 7,724,875 B2
(45) Date of Patent: May 25, 2010

(54) IMAGE GUIDED ACQUISITION OF QUANTITATIVE DUAL ENERGY DATA

(75) Inventors: Kadri Nazar Jabri, Waukesha, WI (US); Rowland Frederick Saunders, Hartland, WI (US); John Michael Sabol, Sussex, WI (US); Gopal Biligeri Avinash, Menomonee, WI (US)

(73) Assignee: General Electric Company, Niskayuna, NY (US)

( * ) Notice: Subject to any disclaimer, the term of this patent is extended or adjusted under 35 U.S.C. 154(b) by 174 days.

(21) Appl. No.: 11/875,427

(22) Filed: Oct. 19, 2007

(65) Prior Publication Data

US 2009/0103679 A1 Apr. 23, 2009

(51) Int. Cl.
*G01N 23/04* (2006.01)
*G01N 23/087* (2006.01)

(52) U.S. Cl. .............................. 378/98.9; 378/5; 378/62

(58) Field of Classification Search .................... 378/54, 378/55, 58, 62, 98.4, 98.8, 98.9, 98.11, 114–116, 378/146, 205
See application file for complete search history.

(56) References Cited

U.S. PATENT DOCUMENTS 5,182,764 A * 1/1993 Peschmann et al. ........... 378/57
5,228,068 A    7/1993 Mazess
5,305,368 A    4/1994 Bisek et al.
6,501,819 B2 * 12/2002 Unger et al. .................... 378/5
6,950,492 B2 *  9/2005 Besson .......................... 378/5
7,085,343 B2 *  8/2006 Shinno et al. .................. 378/9
7,583,782 B2 *  9/2009 Yamazaki ...................... 378/4

* cited by examiner

*Primary Examiner*—Edward J Glick
*Assistant Examiner*—Thomas R Artman
(74) *Attorney, Agent, or Firm*—Fletcher Yoder

(57) ABSTRACT

A technique for establishing texture metrics and bone mineral density (BMD) within an anatomical region of interest. A digital imaging system is used to acquire a standard digital X-ray image with a wide field of view. The standard digital X-ray image is used to guide the imaging system to obtain an image of a region of interest. The standard digital X-ray image is used to calculate various texture metrics, such as a length of a fracture. A dual-energy digital X-ray image of the region of interest is acquired. The dual-energy digital X-ray image is corrected for scatter. The BMD of the region of interest may be established from the scatter-corrected dual-energy digital X-ray image. The BMD, the texture metrics, and/or the scatter-corrected dual-energy X-ray image may be displayed on the standard digital X-ray image.

25 Claims, 5 Drawing Sheets

IMAGE GUIDED ACQUISITION OF QUANTITATIVE DUAL ENERGY DATA

BACKGROUND

The invention relates generally to medical imaging. In particular, the invention relates to digital X-ray medical imaging systems having a flat-panel digital X-ray detector.

The bone mineral density (BMD) of a bone reflects the strength of the bone as represented by calcium content. It is defined as the integral mass of bone mineral per unit of projected area in grams per square centimeter. BMD is a useful tool for the diagnosis and treatment of several diseases and conditions, one of which is osteoporosis.

Osteoporosis is a disease of bone in which the BMD is reduced due to depletion of calcium and bone protein. Osteoporosis predisposes a person to fractures, which are often slow to heal and heal poorly. It is more common in older adults, particularly post-menopausal women; in patients on steroids; and in those who take steroidal drugs. Unchecked osteoporosis can lead to changes in posture, physical abnormality (particularly a condition known colloquially as "dowager's hump"), and decreased mobility. Treatment of osteoporosis includes ensuring that the patient's diet contains adequate calcium and other minerals needed to promote new bone growth, and for post-menopausal women, estrogen or combination hormone supplements.

Dual-energy X-ray absorptiometry (DXA or DEXA) is an increasingly important bone density measurement technology. In fact, osteoporosis is defined by the World Health Organization (WHO) as a BMD having a value 2.5 standard deviations below peak bone mass (in a 20-year-old sex-matched healthy person average) as measured by DXA. The fundamental principle behind DXA is the measurement of the transmission of X-rays with two different energy levels. By measuring how much X-ray energy is transmitted through the patient, the amount of X-ray energy that is absorbed in the patient can be determined. Soft tissues and bone absorb the two energy level X-rays to different degrees. As a result, the absorption of X-rays by the soft tissue may be distinguished from the absorption of X-rays by bone. The soft tissue image data may then be subtracted from the bone image data, leaving only the image data for bone. The BMD is then determined from the bone image data.

However, a BMD alone may not be sufficient for treatment. Evidence of spinal fractures is another important indicator of bone conditions. Determining whether a fracture is present is important both for treatment and for research purposes. A patient may display a reduced BMD, but a physician may be hesitant or unwilling to begin a particular treatment without a diagnosis of a fracture or a deformity. In a research setting, a diagnosis of fracture is important in studying the incidence and prevalence of osteoporosis in a population, as an entry criterion to a clinical study, or as a measure of efficacy with regard to a particular treatment. In fact, the European Foundation for Osteoporosis has published guidelines for clinical trials in osteoporosis which recommends a definition of osteoporosis as "a disorder where one or more fractures have arisen due to an increase in the fragility of bone." In addition, they propose that studies of the efficacy of new drugs used in treatment of osteoporosis have fracture reduction as their clinical endpoint.

While the presence or absence of vertebral fracture is critical in the diagnosis of osteoporosis, diagnosis of vertebral fracture is often difficult. Over one-half of such fractures are asymptomatic, and in cases of minimal symptoms obvious fracture or deformity will often not be observed, particularly if there is no previous radiological record for comparison. Vertebral morphometry techniques promise to make the determination of vertebral fracture or deformation more objective. These approaches rely on certain indexes or normative values of vertebral body dimensions. In using vertebral morphometry to diagnose fractures, the clinician commonly employs analog radiological imaging techniques. In essence, an analog or digital X-ray image of the patient's vertebrae is taken, and printed onto a fixed media, such as an X-ray radiographic film print. The print is made to a specific scale relative to the patient, e.g., one-to-one, or a specifically reduced or expanded scale. Then the clinician manually measures the size of a vertebra by using a ruler and a straight edge and actually draws on the film to outline the vertebral body, and then measures with the ruler between criteria lines drawn onto the film itself.

There have been recent efforts to computerize this morphometric technique. These efforts still rely on first obtaining an analog X-ray image of the vertebra, digitizing the analog image and then manually selecting the points of measurement. Thus the clinician diagnosing or treating osteoporosis must, at a minimum, use two relatively expensive medical devices: a bone densitometer and an X-ray imaging device. Further, morphometric techniques which rely on analog or digital radiography are complicated by image magnification. The analog/digital radiographic image is typically 10-15% larger than life-size, and the magnification is variable depending on the location of the object relative to the plane of the radiograph. In particular, the front edge of the object, away from the radiographic plate is more magnified than the back edge toward the radiographic plate. The result is that bone edges perpendicular to the plane of the plate, which for morphological measurement should produce a sharp visual demarcation on the fan beam radiograph produce a blurred boundary. Distortions of the spine are particularly acute for cone beam exposures at the edges of the cone beam where the beam is most angled. For vertebral morphology the angulation obscures and distorts intervertebral spacing at the top and bottom of a field rendering morphological measurements imprecise. This impreciseness is exacerbated by the imposition of human error when it is left to the clinician to manually select the measurement point. In addition, variation will often necessarily exist between clinicians and between measurements by the same clinician at different times.

While bone densitometers are capable of generating images, the image quality of these present day bone densitometers is inferior to that of common analog or digital X-ray imaging systems. This is particularly true for scanning systems where resolution is intentionally limited to prevent the need for an overly long scanning time. Thus, the imaging capability of bone densitometers has not been relied on for diagnostic purposes and until the present invention, bone densitometry systems have not been used to determine bone morphology, or to analyze the relationships of bone structures. In addition, there is a need to perform the bone densitometry in the same radiology room using the similar acquisition conditions including the magnification and resolution etc. Unfortunately, a diagnostic X-ray image is also not quantitative due to the scatter present in image.

Therefore, a need exists for a technique that combines the beneficial aspects of a diagnostic X-ray image with the quantitative information provided by a BMD acquisition.

BRIEF DESCRIPTION

A technique is presented that combines the beneficial aspects of a diagnostic X-ray image with the quantitative information provided by a BMD acquisition. The technique utilizes a dual-energy X-ray imaging system. The system is used to acquire a standard digital X-ray image. The standard digital X-ray image is used to guide the system to obtain an image of a region of interest. In addition, the standard digital X-ray image is used to calculate various texture and morphometric parameters, such as the lengths of fractures. The dual-energy digital X-ray imaging system is used to acquire dual-energy images of the region of interest. A flat-panel digital X-ray detector detects the X-rays passing through the patient region of interest and produces data representative of the intensity of the X-rays reaching the detector. After correcting the image intensity data for scatter, the image intensity data for each portion of the patient region of interest is combined to form one or more images of the region of interest. The BMD may be established from the scatter-corrected image intensity data. The BMD and the texture metrics may be displayed on the standard digital X-ray image, as well as one or more dual-energy images.

DRAWINGS

These and other features, aspects, and advantages of the present invention will become better understood when the following detailed description is read with reference to the accompanying drawings in which like characters represent like parts throughout the drawings, wherein.

DETAILED DESCRIPTION

Figure 1:
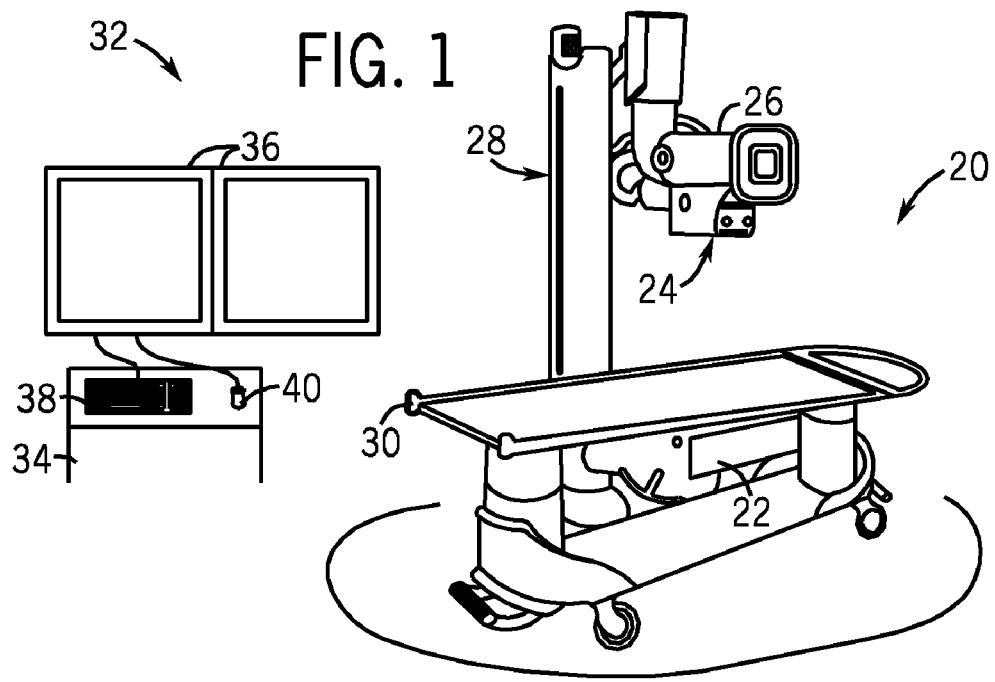
FIG. 1 is a schematic view of a dual-energy X-ray medical imaging system having a collimator and a large, flat-panel digital X-ray detector, in accordance with an exemplary embodiment of the present technique.

Referring now to FIG. 1, the present invention will be described as it might be applied in conjunction with an exemplary imaging system, in this case a dual-energy X-ray imaging system, represented generally by reference numeral 20. In the illustrated embodiment, the dual-energy X-ray imaging system 20 is operable to perform dual-energy X-ray absorpiometry (DXA). In general, however, it should be borne in mind that the present techniques may be used with any suitable imaging modality. In particular, this technique is applicable for any imaging system using a large, flat-panel digital detector. In addition, BMD can be established using other techniques.

In the illustrated embodiment, the system 20 has a large, flat-panel digital X-ray detector 22, and a collimator 24 that may be disposed over an X-ray source 26. Images may be obtained using the full field of view of the system 20. Alternatively, the field of view of the system 20 may be reduced by using the collimator 24 to reduce the spread of X-rays produced by the X-ray source 26. As will be discussed in more detail below, the collimator 24 also is used to reduce the effect of scatter in the images produced by the system 20. The collimator 24 can be placed over the X-ray source 26 as desired or the collimator 24 may be kept disposed over the X-ray source 26. In the illustrated embodiment, the collimator 24 is adjustable so that full (or wide) field of view and reduced (or narrow) field of view images may be obtained with the collimator 24 disposed over the X-ray source 26. In this embodiment, the collimator 24 is a slit collimator. However, the present technique may be used in imaging systems other than those using a slit collimator 24. For example, the present technique may be used in an imaging system having a standard collimator or no collimator, at all.

The dual-energy digital X-ray imaging system 20 is capable of producing an image of a region of interest using X-rays having a first energy level and then producing an image of a region of interest using X-rays having a second energy level. The dual-energy X-ray imaging system 20 is capable of producing separate images of bone and soft tissue using the X-rays of differing energy levels. In this embodiment, the X-rays produced at the first energy level are lower in energy than the X-rays produced at the second energy level. The two images may be combined digitally. Soft tissues and bone absorb the lower energy X-rays and the higher energy X-rays to different degrees, enabling the system 20 to distinguish the absorption of X-rays caused by soft tissue and the absorption caused by bone.

In addition, the dual-energy digital X-ray imaging system is able to acquire standard digital X-ray images. The standard digital X-ray images are acquired with a single exposure of X-rays of a single energy. In addition, the standard digital X-ray images are acquired with the collimator 24 fully open so that it does not affect the image. However, the standard digital X-ray images may be obtained with the collimator 24 in a less than fully open position.

In the illustrated embodiment, the flat-panel digital X-ray detector 22 is an amorphous silicon flat panel that has the ability to acquire two images in rapid succession. This image acquisition speed enables high and low energy images with large energy separation (up to 90 kVp) translating to improved image subtraction. In this embodiment, the detector 22 and X-ray source 26 of the dual-energy X-ray imaging system 20 are mounted on a tilting wall stand 28. As will be discussed in more detail below, instead of exposing the entire surface area of the detector 22 at once, the collimator 24 is used to take an image strip using a smaller portion of the detector 22. The tilting wall stand 28 is adapted to pivot the X-ray source 26 and collimator 24 to enable the system to take a series of image strips that are then combined together digitally to form a larger image. The system 20 also utilizes a mobile stretcher or table 30 upon which patients may lie during imaging procedures. Alternatively, the system may be configured with the flat-panel digital X-ray detector 22 and X-ray source 26 secured to different supports. For example, the flat-panel digital X-ray detector 22 may be secured to a stand that enables the detector 22 to be oriented vertically, while the X-ray source 26 is suspended from the ceiling using a separate support. In addition, the illustrated embodiment of the system 20 has an operator station 32 that uses a computer 34 to control the system 20 and to process the images. The operator's station 32 includes two monitors 36, a keyboard 38, and a mouse 40 in this embodiment to facilitate interactions between the system 20 and a user.

Figure 2:
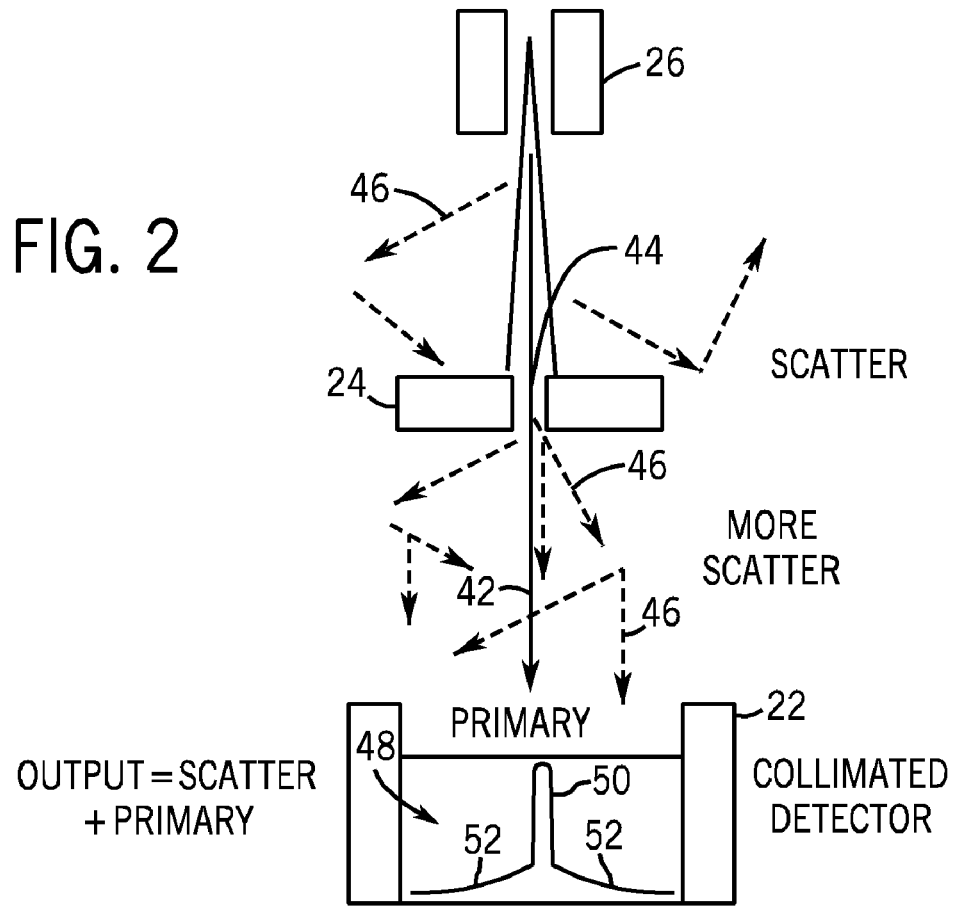
FIG. 2 is a diagrammatical representation of the X-ray source, collimator, and large, flat-panel digital X-ray detector of FIG. 1, in accordance with an exemplary embodiment of the present technique.

Referring generally to FIG. 2, the collimator 24 is used to produce a more accurate image of the patient by reducing the effect of scatter. Ideally, the only X-rays that strike the detector 22 are X-rays that have traveled from the X-ray source 26 through a patient to the detector 22 in a direct path. The X-rays that travel in the desired path are known as "primary" X-rays 42. The primary X-rays 42 are able to pass through a slit 44 in the collimator 24. The collimator 24 blocks stray X-rays produced by the X-ray source 26 from striking the patient. However, other X-rays that are detected by the detector 22 do not follow this direct path. These X-rays are known as scatter 46. Primarily, scatter 46 is X-rays that have interacted with the tissues of the patient and been deflected or redirected from their original path.

Scatter has the effect of skewing the results of the detection of absorption and attenuation of X-rays within the subject. The detector 22 has pixels that detect both primary X-rays 42 and scatter 46. To the pixel of the detector 22 that is in line with the original path of the X-ray, a scattered X-ray would appear to have been absorbed. On the other hand, to the pixel of the detector 22 that detects the scattered X-ray, the scattered X-ray would appear to have passed directly through the patient normally. In each case, the scatter has induced error into the image intensity data and, thus, the medical image. This error reduces contrast in the image, and may appear as fuzziness in the image, and may adversely affect analyses performed based upon the image data.

A representative plot of the image intensity data, referenced generally by reference numeral 48, detected by the detector 22 is presented graphically on the detector 22. The greatest intensity within the image intensity data 48 occurs in the region of the detector 22 that is directly opposite of the slit 44. This region, represented generally by reference numeral 50, of the image intensity data 48 is due to the detection of both primary X-rays 42 and scatter 46 by the detector 22. The sloped intensities, referenced generally by reference numeral 52, in the image intensity data 48 represent the detection of scatter only. These "scatter-only" regions 52 of the image intensity data 48 do not represent the detection of any primary X-rays 42 because the collimator 24 blocks the primary X-rays 42 from reaching the corresponding portions of the detector 22. However, the intensity in the scatter-only regions of the image intensity data 48 is used to estimate the scatter in the region 50 of the image intensity data 48 that is due to the detection of both primary X-rays 42 and scatter 46. The estimated scatter is then subtracted from the region 50 of the image intensity data 48 that is due to the detection of both primary X-rays 42 and scatter 46, leaving image intensity data 48 due to primary X-rays 42 only.

Figure 3:
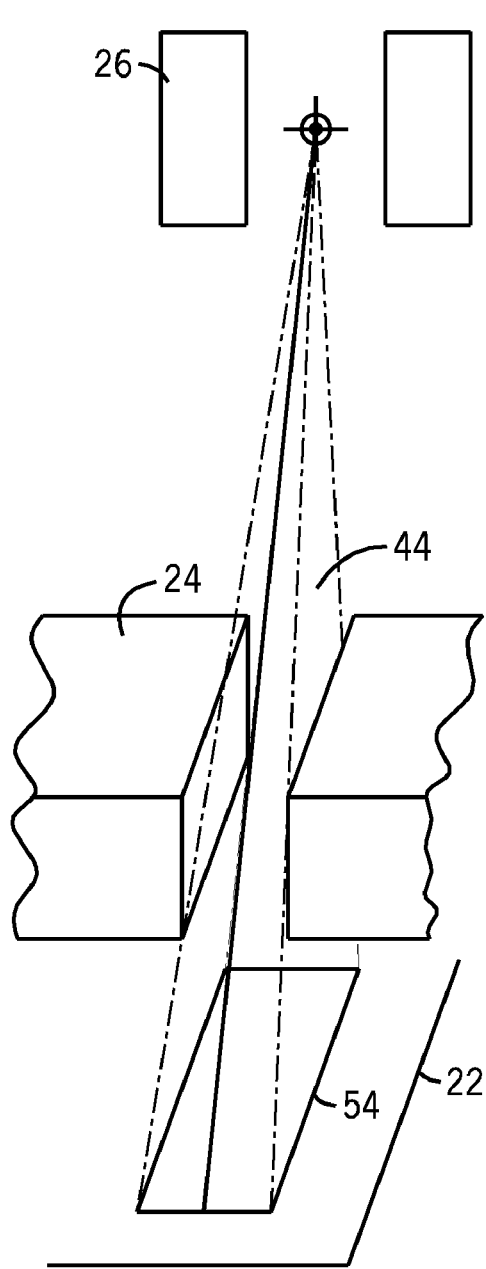
FIGS. 3 and 4 are three-dimensional views of the X-ray source and collimator of FIG. 2, in accordance with an exemplary embodiment of the present technique.
Figure 4:
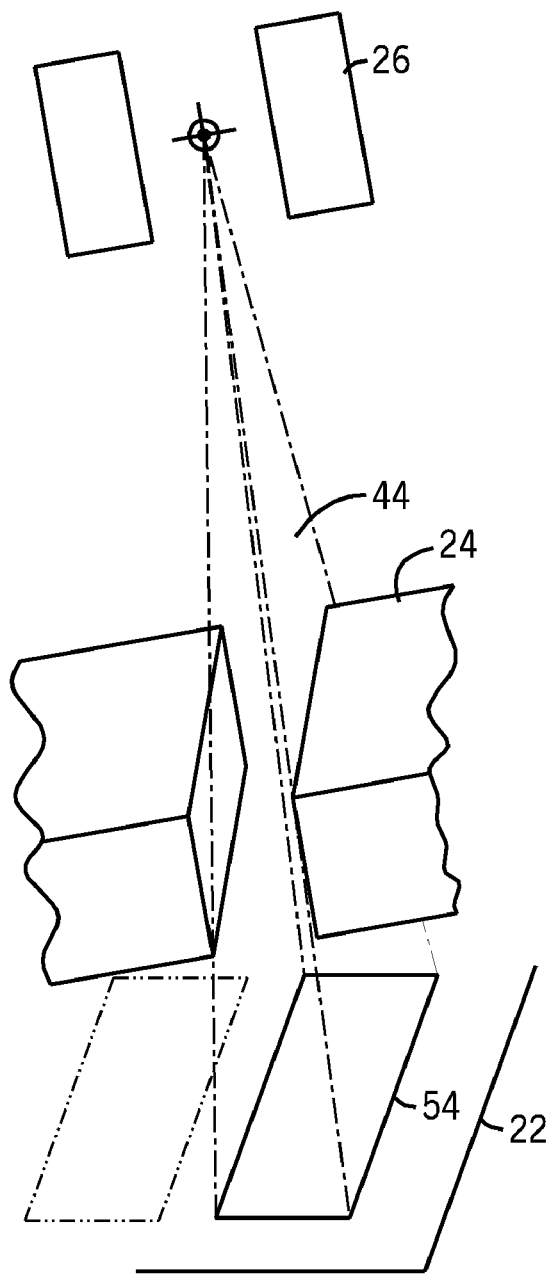

Referring generally to FIGS. 3 and 4, the X-ray source 26 and collimator 24 of the illustrated embodiment combine to form a rectangular image exposure area, as designated generally by reference numeral 54. However, the X-ray source 26 and collimator 24 may be adapted to produce exposure areas having other shapes and sizes. In addition, in this embodiment of the system 20, the slit 44 is approximately 2.5 cm in width. If an image larger than the size of a single exposure area is desired, the tilting structure, such as a wall stand 28 can be used to pivot the X-ray source 26 and collimator 24 to move the rectangular exposure area 54 over the desired exposure area. In the illustrated embodiment, the X-ray source 26 and collimator 24 are shown pivoting from a first position in FIG. 3 to a second position in FIG. 4. In this manner, the rectangular exposure area 54 is moved over the surface of the detector 22 so as to enable the system 20 to take a series of images that are combined digitally to form an image or images of the region of interest as a whole. There may be some overlap of portions of the detector 22 from one exposure to the next. In addition, the system may be configured to pivot to one position and then take both the higher and lower energy level images or the system 20 may go through a complete sequence of images with X-rays at one energy level and then repeat the sequence with X-rays at the other energy level.

As will be appreciated by those skilled in the art, various methodologies may be used in practice for generating image data at different energy levels. For example, with the system in each position, image data at both energy levels may be acquired, or the various positions may be traversed to acquire image data at one energy level, and then the same positions may be repeated to acquire image data at the second energy level. Still further, if the system includes a dual energy detector capable of acquiring image data at two different energy levels simultaneously, combined acquisition at the energy levels may be performed.

Figure 5:
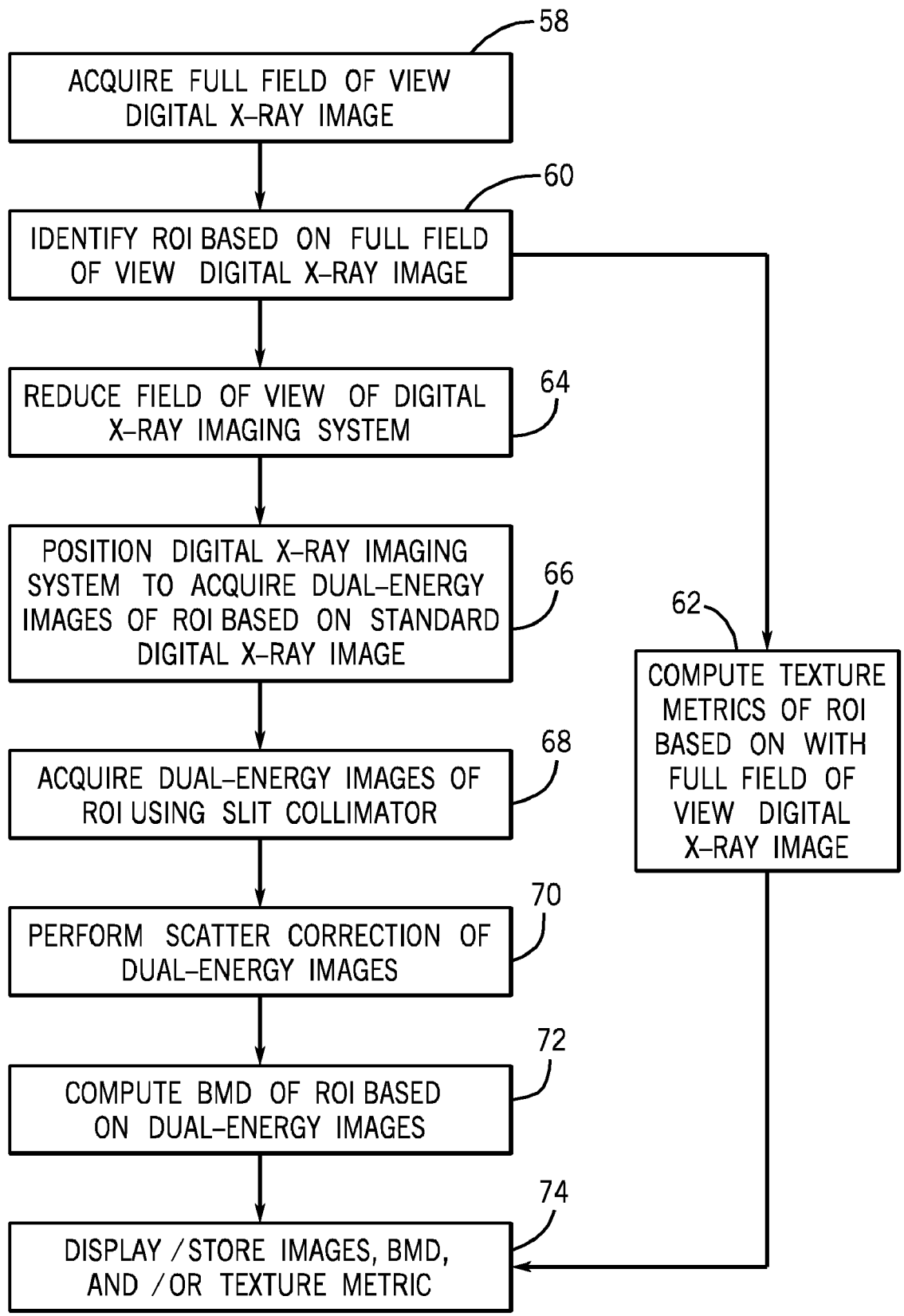
FIG. 5 is a block diagram of a process for using a large field of view image to guide the dual energy X-ray medical imaging system in acquiring a narrower field of view image, in accordance with an exemplary embodiment of the present technique.

Referring generally to FIG. 5, a block diagram of a technique for measuring texture metrics in bone and establishing a patient BMD using the dual-energy X-ray imaging system 20 is provided, and as represented generally by reference numeral 56. In the illustrated embodiment, a full field of view digital X-ray image is taken of a desired anatomical region, as represented generally by reference numeral 58. An example of a desired anatomical region is a hip joint or the lumbar spine. In the illustrated embodiment, the full field of view digital X-ray image is a single-energy X-ray image. However, a full field of view dual-energy digital X-ray image may also be used, rather than a single-energy digital X-ray image.

In the illustrated embodiment, the full field of view image is used to identify one or more anatomical regions of interest, as represented generally by block 60. To aid in identifying the desired region or regions of interest, the single-energy X-ray image may be segmented with, or without, user interaction. If the full field of view image is a dual-energy digital X-ray image, dual-energy decomposition or subtraction may be performed to facilitate the identification of the desired region of interest.

The full field of view image also is used to compute texture metrics of the bone in the region, or regions of interest, as represented generally by reference numeral 62. For example, the full field of view image can be used to measure the length and number of fractures in a bone. Various techniques may be used to measure the length of a fracture. In the illustrated embodiment, the length of a fracture is measured digitally from the full field of view digital X-ray image. For example, a user may trace the fracture as displayed on one of the monitors 36 of the system 20 by using a mouse 40 or other input device to direct the movement of a cursor displayed on the monitor 36. The system 20 is able to calculate the length of the fracture from the movement of the mouse 40 as it traces the length of the fracture. In addition to measuring the length of a fracture, other texture metrics are known and may be obtained using the full field of view image. The full field of view image may also be used to analyze the trabecular structure of bone.

In the illustrated embodiment, the field of view of the imaging system 20 is reduced to acquire dual-energy digital X-ray images of the desired region of interest, as represented generally by block 64. However, the field of view can be reduced to acquire standard digital X-ray images, as well. To reduce the field of view, the collimator 24 is adjusted to reduce the slit 44 size to a desired dimension. Dual-energy digital X-ray images will then be acquired using the reduced field of view of the system 20. By reducing the field of view of the system 20, the exposure to the patient during the acquisition of the dual-energy images is reduced. As will be discussed in more detail below, the reduced field of view of the digital X-ray system 20 also enables a scatter-correction procedure to be performed on the images.

The standard X-ray image is used to guide the X-ray source 26 and collimator 24 into the proper position to acquire the dual-energy images of the desired region of interest, as represented generally by block 66. After locating the region of interest in the standard digital X-ray image, as displayed on a monitor 36, a user may use the mouse 40 to place a window or other mark on the region, or regions, of interest in the standard digital X-ray image displayed on a monitor 36. The dual-energy X-ray imaging system 20 will align the X-ray source 26 and collimator 24 with the window or mark. In the illustrated embodiment, the region of interest is smaller than the reduced field of view image. However, when the region of interest is larger than the reduced field of view, multiple slot scans of the patient may be performed. The multiple slot scans can be combined digitally to produce a single image. In addition, as noted above, dual-energy digital X-ray images may be obtained for a plurality of regions of interest. The user can use the mouse 40 to select as many regions of interest for imaging as desired. Alternatively, a program may be used to identify a region of interest in the standard digital X-ray image and to direct the X-ray source 26 and collimator 24 to the proper position to acquire the dual-energy image of the desired region of interest automatically. For example, a segmentation program may be used to identify the region of interest and direct the X-ray source 26 and collimator 24 into the proper position to acquire the dual-energy images of the desired region of interest. The segmentation program may be adapted to identify landmarks or may use an anatomical atlas to locate the region of interest. Other methods may also be used.

After the system 20 is oriented properly, a dual-energy image set of the region of interest is acquired, as represented generally by block 68. A first image with the reduced field of view is acquired with X-rays having a first energy. A second image with the reduced field of view is then acquired with X-rays having a second energy. Typically, the second X-rays are greater in energy than the first X-rays when acquiring images with a dual-energy digital X-ray imaging system. The two images are then combined to produce one or more images. In addition, as noted above, the region of interest may be greater in size than the narrower field of view. In this event, images may be acquired of one or more contiguous or overlapping regions at multiple energies and then pasted together to obtain a dual or multi-energy data set.

The dual-energy digital X-ray imaging system 20 corrects the image intensity data in the dual-energy image set for scatter, as represented generally by block 70. Because of the reduced field of view, a portion of the detector 22 will receive X-rays that are the result of scatter only. The illustrated embodiment of the system 20 utilizes a scatter correction technique to reduce the effect of scatter on images formed by the system 20 by identifying the regions 52 of the image intensity data 48 that are the products of scatter 46 only and then using the intensity of the scatter in these regions to estimate the intensity of the scatter 46 within the region 50 of the image intensity data 48 that is the product of both primary X-rays 42 and scatter 46. This technique is described in more detail in the application entitled: "Slit Collimator Scatter Correction," Ser. No. 11/866,878, filed on Oct. 3, 2007, which is hereby incorporated by reference. Furthermore, the only region of the image intensity data 48 that is used to form an image is the region 50 of the image intensity data 48 that is the product of both primary X-rays 42 and scatter 46. In this embodiment of the technique, the image intensity data 48 is corrected by subtracting the scatter intensity from the image intensity data 48, leaving behind only the image intensity data 48 that is the product of primary X-rays 42. In addition, other corrections that facilitate quantitative data extraction from the image data set may be performed.

The BMD is then established using the scatter-corrected image intensity data, as represented generally by block 70. In addition, quantitative measurements other than a BMD may be performed on the scatter-corrected image intensity data. For example, cardiac calcification measurements may be obtained from the scatter-corrected image intensity data.

The reduced field of view image, the BMD, and the texture metrics may be displayed on the standard digital X-ray image, as represented generally by reference numeral 72. The texture metrics are included with the BMD readings to provide structural information in addition to the composition information obtained from the BMD. The combination of the texture metrics, the BMD information, the standard digital X-ray image having a full field of view, along with the dual-energy digital X-ray image having a reduced field of view may enable more reliable treatments for osteoporosis.

In addition, the full field of view image, the reduced field of view image, the BMD, and the texture metrics are stored for later retrieval, as represented generally by block 74. The data may be stored in the dual-energy X-ray imaging system 20 or sent to a PACS or similar archiving system.

Figure 6:
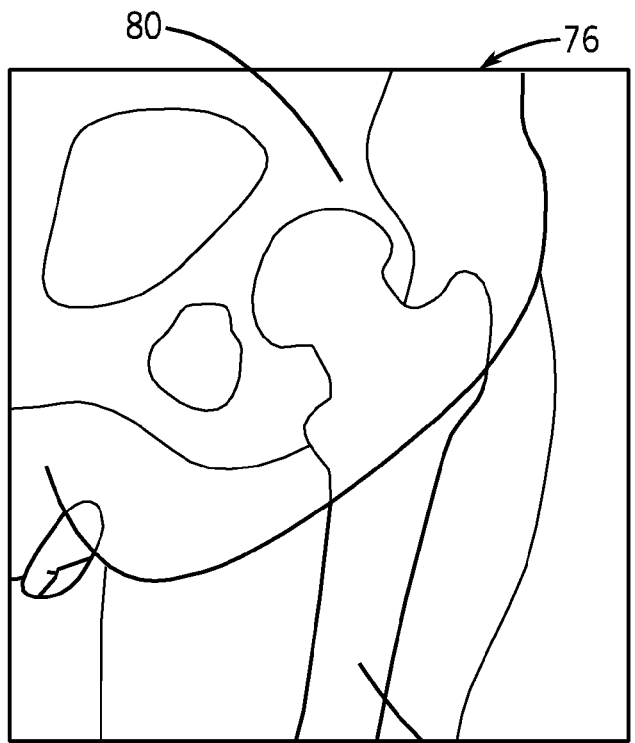
FIG. 6 is a large field of view image of a hip joint, in accordance with an exemplary embodiment of the present technique.

Referring generally to FIG. 6, a standard digital X-ray image of a patient hip joint obtained with the system 20 configured to acquire an image with the full field of view of the system 20 is presented, as represented generally by reference numeral 76. The bones of interest in the standard digital X-ray image are the femur 78 and the hipbone 80. Texture metrics, such as the length of any fractures, can be established from this full field of view digital X-ray image 76.

Figure 7:
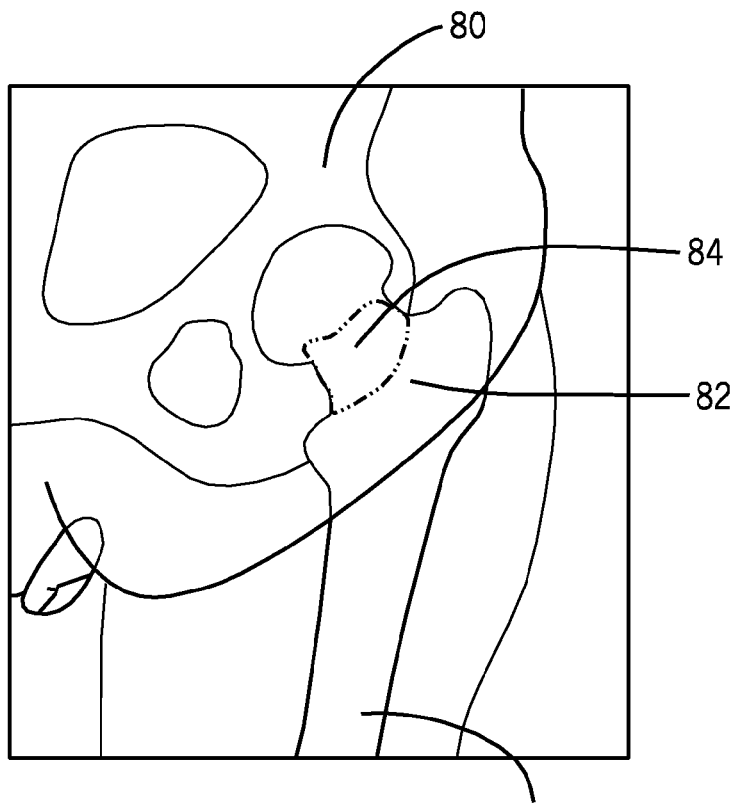
FIG. 7 is the large field of view image of FIG. 6 with an anatomical region of interest in the head of a femur marked, in accordance with an exemplary embodiment of the present technique.

Referring generally to FIG. 7, a region of interest 82 in the full field of view digital X-ray image 76 of a patient's hip is marked with a dashed line. In the illustrated embodiment, the region of interest 82 is a portion of the head 84 of the femur 78.

Figure 8:
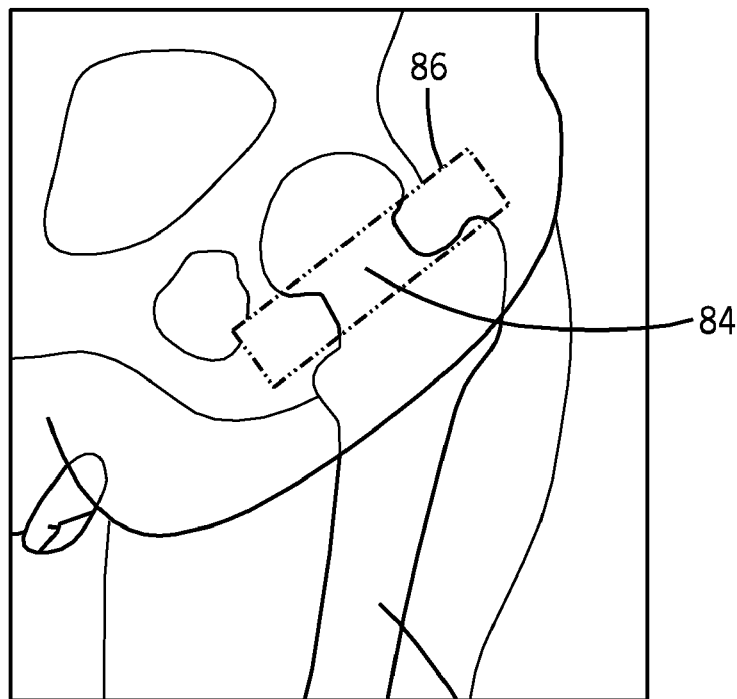
FIG. 8 is the large field of view image of FIG. 6 with a guide representative of the narrower field of view disposed over the anatomical region of interest, in accordance with an exemplary embodiment of the present technique.

Referring generally to FIG. 8, an operator uses the full field of view digital X-ray image 76 to position a reduced field of view image window 86 over the region of interest 82 in this embodiment of the technique. The reduced field of view image window 86 is used to direct the dual-energy digital X-ray imaging system 20 to the desired location for acquiring a reduced field of view dual-energy digital X-ray image. The dual-energy digital X-ray imaging system 20 reduces the field of view as directed and positions the X-ray source 26 and collimator 24 to obtain the desired reduced field of view dual-energy digital X-ray image. The dual-energy digital X-ray detector 22 remains stationary, while the X-ray source 26 and collimator 24 are moved into position relative to the detector 22.

Figure 9:
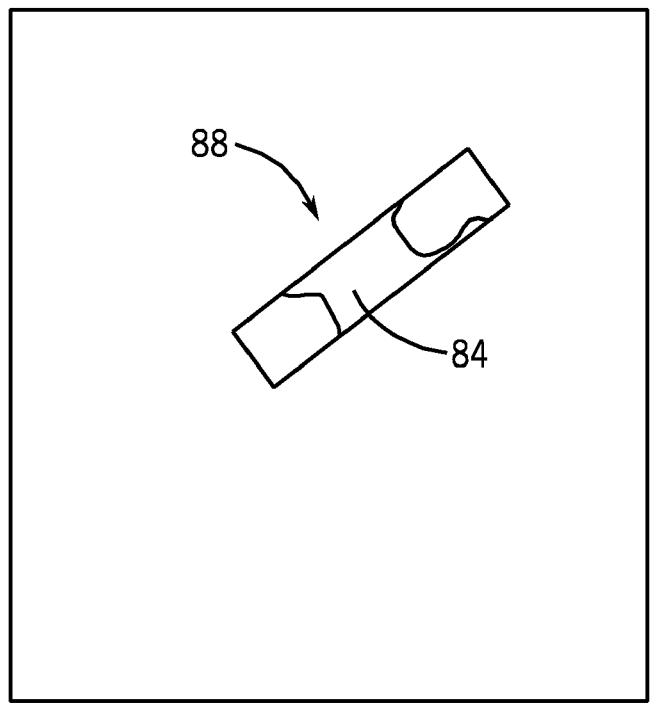
FIG. 9 is a dual-energy image having a narrow field of view of the anatomical region of interest, in accordance with an exemplary embodiment of the present technique.

Referring generally to FIG. 9, the dual-energy digital X-ray imaging system 20 produces a reduced field of view dual-energy digital X-ray image, represented generally by reference numeral 88. In this example, the image is of the head 84 of the femur 78. The reduced field of view dual-energy digital X-ray image 88 is corrected for scatter as described above and the BMD is established therefrom. As discussed above, the BMD can be overlaid or annotated on the standard digital X-ray image 76 or the reduced field of view dual-energy digital X-ray image 88. In addition, the reduced field of view dual-energy digital X-ray image 88 may be inserted into the full field of view digital X-ray image 76, such as to occupy the space occupied by the reduced field of view image window 86 in FIG. 8. The texture metrics may be established from the reduced field of view dual-energy digital X-ray image 88, instead of the standard digital X-ray image 76. In addition, any texture metrics, such as fracture length, may be overlaid or annotated on the standard digital X-ray image 76 or the reduced field of view dual-energy digital X-ray image 88.

While only certain features of the invention have been illustrated and described herein, many modifications and changes will occur to those skilled in the art. It is, therefore, to be understood that the appended claims are intended to cover all such modifications and changes as fall within the true spirit of the invention.

The invention claimed is:

1. A computer-implemented method for processing image data, comprising:
   acquiring a digital X-ray image having a first field of view using a digital X-ray imaging system;
   identifying a region of interest in the digital X-ray image having a first field of view;
   positioning the digital X-ray imaging system to acquire an image of the region of interest with the digital X-ray imaging system reconfigured to acquire a digital X-ray image with a second field of view, the second field of view being different from the first field of view; and
   acquiring a dual-energy digital X-ray image of the region of interest with the digital X-ray imaging system reconfigured to acquire a digital X-ray image with the second field of view.

2. The computer-implemented method for processing image data as recited in claim 1, wherein acquiring a digital X-ray image having a first field of view using a digital X-ray imaging system comprises opening a slit of a collimator disposed over an X-ray source of the digital X-ray imaging system to a fully open position.

3. The computer-implemented method for processing image data as recited in claim 1, comprising:
   establishing a quantitative metric of an object of interest based on the digital X-ray image having a first field of view.

4. The computer-implemented method for processing image data as recited in claim 1, wherein reconfiguring the digital X-ray imaging system comprises disposing a collimator over an X-ray source.

5. The computer-implemented method for processing image data as recited in claim 1, wherein acquiring a digital X-ray image having a first field of view using a digital X-ray imaging system comprises acquiring a digital X-ray image using X-rays substantially of a single energy level.

6. The computer-implemented method for processing image data as recited in claim 1, wherein the digital X-ray imaging system comprises a dual-energy X-ray source, a collimator, and a dual-energy digital X-ray detector and positioning the digital X-ray imaging system comprises orienting the dual-energy X-ray source and the collimator relative to the dual-energy digital X-ray detector to position the second field of view at the location on the dual-energy digital X-ray detector corresponding to the region of interest in the digital X-ray image having a first field of view.

7. The computer-implemented method for processing image data as recited in claim 1, comprising correcting the dual-energy digital X-ray image of the region of interest for scatter, wherein the dual-energy digital X-ray image comprises image intensity data having a first region that is produced by primary X-rays and scatter and a second region that is produced by scatter only.

8. The computer-implemented method for processing image data as recited in claim 7, wherein correcting the dual-energy digital X-ray image for scatter comprises:
   identifying within the image intensity data the first region that is produced by primary X-rays and scatter and the second region that is produced by scatter only;
   establishing scatter intensity in the second region of the image intensity data that is produced by scatter only;
   estimating scatter intensity in the first region of the image intensity data based on the scatter intensity in the at least one second region of the image intensity data; and
   correcting the first region of the image intensity data for scatter based on the estimated scatter intensity in the first region.

9. The computer-implemented method for processing image data as recited in claim 7, comprising:
   establishing quantitative information of the region of interest based on a scatter-corrected dual-energy digital X-ray image.

10. The computer-implemented method for processing image data as recited in claim 9, wherein establishing quantitative information of the region of interest based on a scatter-corrected dual-energy digital X-ray image comprises establishing bone mineral density of the region of interest.

11. The computer-implemented method for processing image data as recited in claim 1, wherein identifying a region of interest in the digital X-ray image having a first field of view comprises guiding the digital X-ray imaging system to the location of the region of interest within the digital X-ray image.

12. The computer-implemented method for processing image data as recited in claim 11, wherein guiding the digital X-ray imaging system to the location of the region of interest within the digital X-ray image comprises operating a computer input device to dispose a graphical representation on the region of interest in the digital X-ray image as displayed on a monitor of the digital X-ray imaging system.

13. The computer-implemented method for processing image data as recited in claim 11, wherein guiding the digital X-ray imaging system to the location of the region of interest within the digital X-ray image is performed automatically based on a program adapted to identify the region of interest within the digital X-ray image.

14. A system for computer for processing image data, comprising:
   means for acquiring a digital X-ray image having a first field of view using a digital X-ray imaging system;
   means for identifying a region in the digital X-ray image having a first field of view;
   means for positioning the digital X-ray imaging system to acquire an image of the region of interest with the digital X-ray imaging system configured to acquire a digital X-ray image with a second field of view, the second field of view being different from the first field of view; and
   means for acquiring a dual-energy digital X-ray image of the region of interest with the digital X-ray imaging system reconfigured to acquire a digital X-ray image with the second field of view.

15. A machine-readable medium for processing medical image data, comprising:

code operable to acquire a digital X-ray image having a first field of view using a digital X-ray imaging system;

code operable to identify a region of interest in the digital X-ray image having a first field of view;

code operable to position the digital X-ray imaging system to acquire an image of the region of interest with the digital X-ray imaging system configured to acquire a digital X-ray image with a second field of view, the second field of view being different from the first field of view; and code operable to acquire a dual-energy digital X-ray image of the region of interest with the digital X-ray imaging system reconfigured to acquire a digital X-ray image with the second field of view.

16. A computer-implemented method for obtaining a digital X-ray image, comprising:

acquiring a first digital X-ray image with an X-ray source configured to produce an image having a first field of view;

guiding the X-ray source to a position to acquire an image of a region of interest based on the location of the region of interest in the first digital X-ray image; and acquiring a dual-energy digital X-ray image of the region of interest with the X-ray source reconfigured to produce an image having a second field of view, the second field of view being different from the first field of view.

17. The computer-implemented method for processing image data as recited in claim 16, comprising:

computing a quantitative metric of an object of interest based on the first digital X-ray image.

18. The computer-implemented method for processing image data as recited in claim 16, comprising:

correcting the dual-energy digital X-ray image of the region of interest for scatter.

19. The computer-implemented method for processing image data as recited in claim 18, wherein correcting the dual-energy digital X-ray image of the region of interest for scatter comprises:

identifying a first region of the dual-energy digital X-ray image that is produced by primary X-rays and scatter and a second region that is produced by scatter only;

establishing scatter intensity in the second region of the dual-energy digital X-ray image that is produced by scatter only;

estimating scatter intensity in the first region of the dual-energy digital X-ray image based on the scatter intensity in the second region of the dual-energy digital X-ray image; and correcting the first region of the dual-energy digital X-ray image for scatter based on the estimated scatter intensity in the first region of the dual-energy digital X-ray image.

20. The computer-implemented method for processing image data as recited in claim 19, comprising:

establishing quantitative information of the region of interest based on the dual-energy digital X-ray image of the region of interest corrected for scatter.

21. The computer-implemented method for processing image data as recited in claim 20, wherein establishing quantitative information of the region of interest based on the dual-energy digital X-ray image of the region of interest corrected for scatter comprises establishing bone mineral density in the region of interest.

22. The computer-implemented method for processing image data as recited in claim 16, comprising:

identifying the region of interest in the first digital X-ray image automatically using a program adapted to identify the region of interest in the first digital X-ray image.

23. The computer-implemented method for processing image data as recited in claim 22, wherein guiding the X-ray source to a position to acquire an image of a region of interest based on the location of the region of interest in the first digital X-ray image comprises automatically positioning the X-ray source to acquire the image of the region of interest based on the location of the region of interest in the first digital X-ray image identified by the program adapted to identify the region of interest in the first digital X-ray image.

24. The computer-implemented method for processing image data as recited in claim 22, wherein the program adapted to identify the region of interest in the first digital X-ray image comprises a segmentation program.

25. A computer-implemented method for processing image data, comprising:

acquiring a single-energy digital X-ray image using a digital X-ray imaging system;

identifying a region of interest in the single-energy digital X-ray image;

positioning the digital X-ray imaging system to acquire a dual-energy image of the region of interest; and acquiring a dual-energy digital X-ray image of the region of interest with the digital X-ray imaging system.

* * * * *